United States Patent [19]

Briggs

[11] Plant 5,171

[45] Jan. 3, 1984

[54] TOMATO PLANT

[75] Inventor: Carroll G. Briggs, San Juan Bautista, Calif.

[73] Assignee: The Upjohn Company, Kalamazoo, Mich.

[21] Appl. No.: 340,956

[22] Filed: Jan. 20, 1982

[51] Int. Cl.[3] ..... A01H 5/00

[52] U.S. Cl. ..... Plt./89

[58] Field of Search ..... Plt./89

*Primary Examiner*—Robert E. Bagwill

*Attorney, Agent, or Firm*—Sidney B. Williams, Jr.

[57] ABSTRACT

A new and distinct variety of a hybrid tomato plant substantially as herein shown and described, characterized as to novelty when compared to Flora-Dade, Tempo and Walter, the most similar cultivars to it, by uniform crop characteristics, low grading loss, high yield, large fruit, low percentage of fruit ripening defects and multiple disease resistance and tolerance.

1 Drawing Figure

BACKGROUND OF THE INVENTION

The present invention relates to a new and distinct cultivar of tomato plant, Sunny, which was produced and originated asexually by Carroll Grey Briggs. The plant was propagated by crossing the variety TOM 537 with TOM 540. The former being the seed parent and the latter being the pollen parent.

Their breeding has produced a new and improved cultivar of tomato plant which is distinguished from its parents as well as all other cultivars that I am aware of. The cultivars most similar to it are Flora-Dade, Tempo and Walter. It is distinguished from Flora-Dade by larger fruit, higher yield, pointed pedicels and softer fruit. It is distinguished from Tempo by resistance to *Verticillium dahliae* and firmer fruit. It is distinguished from Walter by larger and firmer fruit, higher yield and resistance to *Verticillium dahliae.*

DRAWINGS

In the drawing, which is a photographic illustration of the new variety, is a view of the fruit and leaves and flowers.

DETAILED DESCRIPTION

A detailed description of my new variety is as follows based upon observation made from plants and fruit grown in California, Florida, the Northeastern and Southeastern United States and Italy.

Type: Determinate market tomato.

Breeding: Seedling.

*Seed parent.*—TOM 537.

*Pollen parent.*—TOM 540.

Propagation: Holds its distinguishing characteristics through succeeding propagation by cuttings.

Plant:

*Habit.*—Determinate in growth habit. Suitable for use as a ground or staked variety — hardy and vigorous.

*Growth.*—Medium-sized plant, similar to Walter.

*Foliage.*—Leaves—Usually compound of about 12 leaflets each when mature. Leaflets: Shape—elliptic with margin teeth.

*Size of leaf (mature)*—Length—about 9.5 cm. Width—about 5.4 cm.

*Color.*—Dark green; similar to Flora-Dade.

*Main stems.*—About 68 cm long.

*Branches.*—About 8 primary branches from main stem.

*New shoots.*—About 5 secondary branches per primary branch.

Fruit:

*Borne.*—Heavily; usually about 128 fruits per plant.

*Shape.*—Deep globe.

*Size.*—Heavy; average weight of 213 gm. Height—about 6.1 cm. Width—about 7.7 cm. Wall thickness about 0.66 cm.

*Texture.*—Thick-meated and firm.

*Color (skin).*—Immature — Light green face with a waxy appearance and medium-dark green shoulders. Mature — Red without streaking or yellow shoulder.

*Color (flesh).*—Deep red.

*Bearing season.*—About 99 days after transplanting, depending on seasonal conditions.

*Flavor.*—Similar to Walter.

*Skin.*—Relatively tough.

Disease resistance: *Verticillium dahliae* strain 1; *Fusarium oxysporum* f. sp. *lycopersici* races 1 and 2; *Stemphyllium solani*; *Alternaria alternia* fs *lycopersici*.

Use: Market fruit for human consumption.

Bearing qualities:

*Quality.*—The primary characteristics referred to have been found to be fixed in the asexual reproduction of the plant.

I claim:

1. A new and distinct variety of a hybrid tomato plant substantially as herein shown and described.

* * * * *

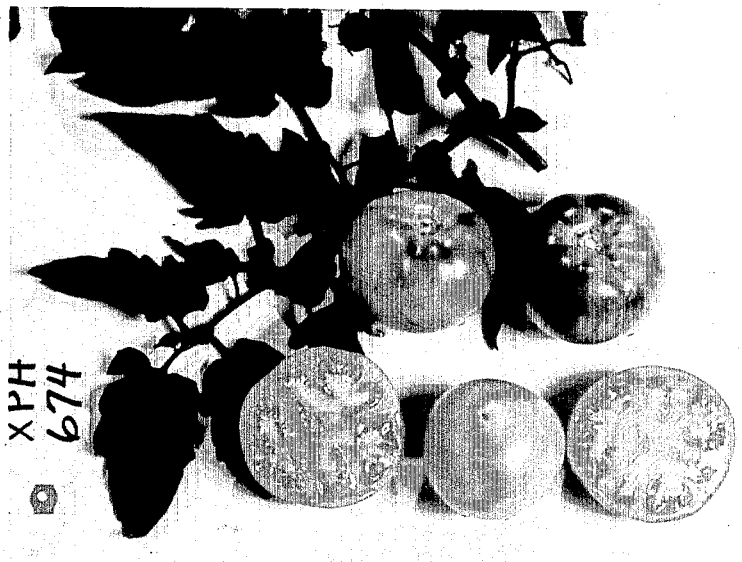
XPH
674